US00PP10061P

Jnited States Patent [19]

ergman

[11] Patent Number: Plant 10,061

[45] Date of Patent: Oct. 14, 1997

4] AZALEA PLANT NAMED MYSTIC

5] Inventor: Wendy R. Bergman, Lehigh Acres, Fla.

3] Assignee: Yoder Brothers, Inc., Barberton, Ohio

1] Appl. No.: 583,474

2] Filed: Jan. 5, 1996

1] Int. Cl.[6] ..... A01H 5/00

2] U.S. Cl. ..... Plt./57

8] Field of Search ..... Plt./55, 56, 57

6] References Cited

PUBLICATIONS

Cox, Peter A., (Listing for) "Mystic" *Dwarf Rhododendrons* 1973 MacMillan Publishing Co., Inc, N.Y., p. 207.

Leach, David G., (Listing for) "Mystic" *Rhododendrons of the World* 1961, Charles Schribner's Sons, N.Y., p. 478.

*Primary Examiner*—James R. Feyrer

*Attorney, Agent, or Firm*—Foley & Lardner

[57] ABSTRACT

An azalea plant named Mystic particularly characterized by its dark glossy evergreen foliage, single flower form, fuchsia flower color, ease of budding, uniform and dense plant habit, free branching, rapid and uniform flower response in a year round controlled program, excellent cooler tolerance and good keeping quality.

1 Drawing Sheet

The present invention comprises a new and distinct cul-'ar of Azalea, a greenhouse forcing type, hereinafter ferred to as Mystic.

Mystic, identified as Code 1010 during the selection ocess, originated from a planned cross hybridization tween two selected breeding lines in a controlled breeding ogram in Fort Myers, Fla.

The female, or seed parent of Mystic is the commercial ltivar Girard's Fuchsia, a deep reddish purple single. The ale, or pollen parent is a seedling known as Code 227, a oprietary breeding line.

Mystic was discovered and selected by Wendy R. Berg-an as one flowering plant within the progeny of the stated oss in January 1992, in Fort Myers, Fla.

The first asexual reproduction of Mystic was accom-ished when vegetative cuttings were taken from the initial lection in Apr. 1992, in Fort Myers, Fla., by technicians orking under formulations established and supervised by endy R. Bergman.

Horticultural examination of controlled flowerings of ccessive generations of plants derived from cuttings taken om the original selection has shown that the unique mbination of characteristics as herein disclosed for Mystic e fixed and retained through successive generations of exual reproduction.

Mystic has not been observed under all possible environ-ental conditions. The phenotype may vary significantly th variations in environment such as temperature, light tensity and day length, without, however, any variance in e genotype. The following observations, measurements d comparisons describe plants that were grown in Fort yers, Fla. in a controlled greenhouse environment and llowing a commercial schedule.

The following traits have been repeatedly observed and e determined to be basic characteristics of Mystic, which, combination, distinguish this azalea as a new and distinct ltivar:

1. A fuchsia flower color (between 71B and 71C) fading a rose pink (between 68A and 68B) at old age.
2. Single flower form.
3. The flowers range in size from 6.5 to 8.5 cm in diameter th 7.5 cm the average size.
4. Compact, uniform and symmetrical plant habit.
5. Fast, uniform response in a year round controlled owering program, forcing in 27 days on average.
6. Good longevity in a simulated home environment, with owers lasting up to 25 days.

7. Excellent foliage retention and no flower bud damage when cooled for six (6) weeks with no lighting at 38° F.

The accompanying color photograph shows in perspective view the unique features of the new cultivar, with colors being as true as possible with color illustrations on this type.

Of the commercial cultivars known to the inventor, the most similar in comparison to Mystic is the seed parent Girard's Fuchsia. While both are evergreen azaleas with single flower form, Mystic's flowers are a shade lighter in color than Girard's Fuchsia and the petal margins of Mystic are not as wavy.

In the following description color references are made to The Royal Horticultural Society Colour Chart. The color values were determined on Apr. 6, 1995. All readings were taken in an office under cool white fluorescent lights, facing a west window between the hours of 10:00 a.m and 2:00 p.m.

Classification:

*Botanical.*—Rhododendron hybrida, evergreen type.

*Commercial.*—Florist forcing pot azalea, cv. Mystic.

INFLORESCENCE

Flower (General):

*Size.*—6.5 to 8.5 cm.

*Born.*—Terminal cluster, usually three (3) per bud, ranging from two to four (2–4). Often more than one (1) bud per stem.

*Form.*—Single. Funnel-form.

*Blooming habit.*—Once profusely. Buds easily and uniformly in a year-round flowering program. The majority of terminal buds break color within one (1) week of the first. Flowering begins approximately 27 days after the start of forcing.

*Fragrance.*—Present.

Corolla (Petals):

*Texture.*—Soft.

*Substance.*—Heavy.

*Shape.*—Rounded. Irregular undulate margin.

*Color (fully open).*—Generally between 71B and 71C. Fuchsia. Upper surface: Edge: Between 71C and 71D. Center: 72C. Base: Between 72D and 73B. Lower surface: 71D with overlay toward base of between 58B and 58C. Blotch: 61A.

Bud:

*Size.*—Medium.

*Shape.*—Conoidal.

*Color.*—Between 71B and 71C.

*Bud sheath.*—Light green to light brown with light brown hairs.

Calyx:

*Form.*—Acuminate.

*Color.*—144B.

Peduncle:

*Length.*—0.5–1.5 cm.

*Strength.*—Strong.

*Aspect.*—Pubescent.

Reproductive organs:

*Androecium* (*stamens*).—Number: Six to eight (6–8). Anthers: 79A. Filaments: Length: 2.3–4.5 cm. Color: Between 66C and 66D.

*Gynoecium* (*pistil*).—Stigma: 59A. Style: Length: 3.0–4.8 cm. Color: Between 73A and 73B. Ovary: Pubescent.

PLANT CHARACTERISTICS

Foliage:

*Type.*—Evergreen.

*Arangement.*—Alternate.

*Shape.*—Elliptic to ovate.

*Size.*—Length: 2.0–7.0 cm. Width: 0.7–3.4 cm.

*Margin.*—Entire.

*Color.*—Immature: Upper surface; 144A. Lower surface: 144B. Mature: Upper surface: 139A. Lower surface: 146B. Texture: Leathery, Tomentum: Present on upper surface, Insignificant.

Stems:

*Color.*—Immature: 184B. Mature: 165A. Tomentum: Present, sparse, Insignificant.

Plant habit: Compact, upright, dense bush which is uniform and symmetrical in a six-inch (6") pot when pinched three (3) times. Total crop time to the dormant budded stage is 40–42 weeks to produce a plant approximately 30 cm in diameter and having a total height of 30–36 cm. Internode lengths vary widely from 1–30 mm on the same stem.

Branching habit: Free branching, producing three to five (3–5) breaks when a vegetative cutting is pinched.

Rooting: Roots easily in eight to ten (8–10) weeks with 75° F. soil temperature.

Budding ease: Plants produce flower buds easily and uniformly year round with the use of commercially available plant growth regulators. Natural season response has not been acertained.

Cooler tolerance: Plants placed in a cooler as a means of breaking dormancy perform very well. Mystic is tolerant of six (6) weeks in an unlighted cooler at 38° F. without excessive bud damage or foliage loss.

Blooming: Plants reach the stage of 12 buds showing color in 27 days on average after the cooling treatment. This varies from 20 to 34 days depending upon time of year. Mystic flowers uniformly and profusely across the plant.

Shelf life: When plants are moved to an office or home environment at the stage of eight (8) open flowers, they maintain an attractive appearance for 25 days on average.

It is claimed:

1. A new and distinct cultivar of azalea named Mystic, as described and illustrated.

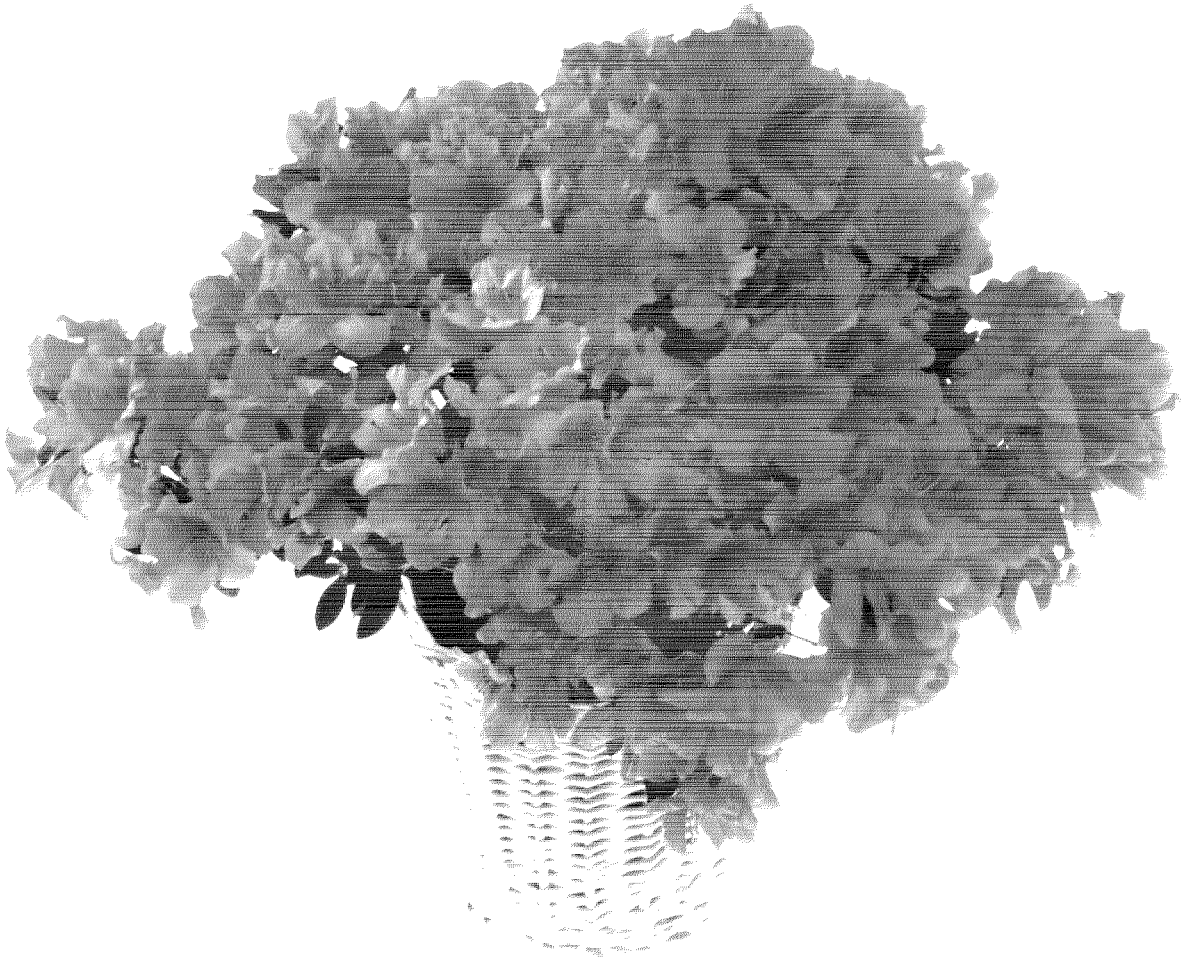

* * * * *